United States Patent [19]

Gross

[11] Patent Number: 4,580,563

[45] Date of Patent: Apr. 8, 1986

[54] ARTHROSCOPIC SURGICAL INSTRUMENT AND METHOD

[76] Inventor: R. Michael Gross, 3559 Woolworth Ave., Omaha, Nebr. 68105

[21] Appl. No.: 544,555

[22] Filed: Oct. 24, 1983

[51] Int. Cl.$^4$ .................. A61B 17/04; A61B 17/32
[52] U.S. Cl. ........................... 128/305; 128/92 E; 128/92 EC; 128/334 R
[58] Field of Search ............ 128/92 EC, 92 B, 92 E, 128/334 R, 304, 305; 604/164; 227/DIG. 1

[56] References Cited

U.S. PATENT DOCUMENTS

| | | | |
|---|---|---|---|
| 4,230,123 | 10/1980 | Hawkins, Jr. | 128/658 |
| 4,263,903 | 4/1981 | Griggs | 128/92 B |
| 4,462,395 | 7/1984 | Johnson | 128/92 EC X |

FOREIGN PATENT DOCUMENTS

| | | | |
|---|---|---|---|
| 735333 | 4/1943 | Fed. Rep. of Germany | 128/92 EC |
| 742097 | 10/1943 | Fed. Rep. of Germany | 128/92 EC |

*Primary Examiner*—Michael H. Thaler
*Attorney, Agent, or Firm*—Zarley, McKee, Thomte, Voorhees & Sease

[57] ABSTRACT

An arthroscopic surgical instrument for repairing capsular disruption associated with shoulder dislocations and subluxations includes an elongated knife, an elongated sleeve which fits telescopically over the knife for sliding movement thereon, a staple adapted for insertion into the sleeve upon removal of the knife and an elongated tamper tool insertable through the sleeve for setting the staple in the shoulder joint.

The orthopedic surgical procedure includes inserting an arthroscope into the shoulder for viewing the insertion of the knife into the shoulder capsule. The sleeve is then advanced down over the knife into the capsule whereupon the knife is withdrawn. The sleeve is then shifted to a position over the scapula bone to make a tuck in the capsule. A staple is then inserted into the sleeve and driven through the tuck into the scapula by a tamper tool. The tamper tool, sleeve and arthroscope are then removed from the shoulder girdle to complete the operation.

23 Claims, 8 Drawing Figures

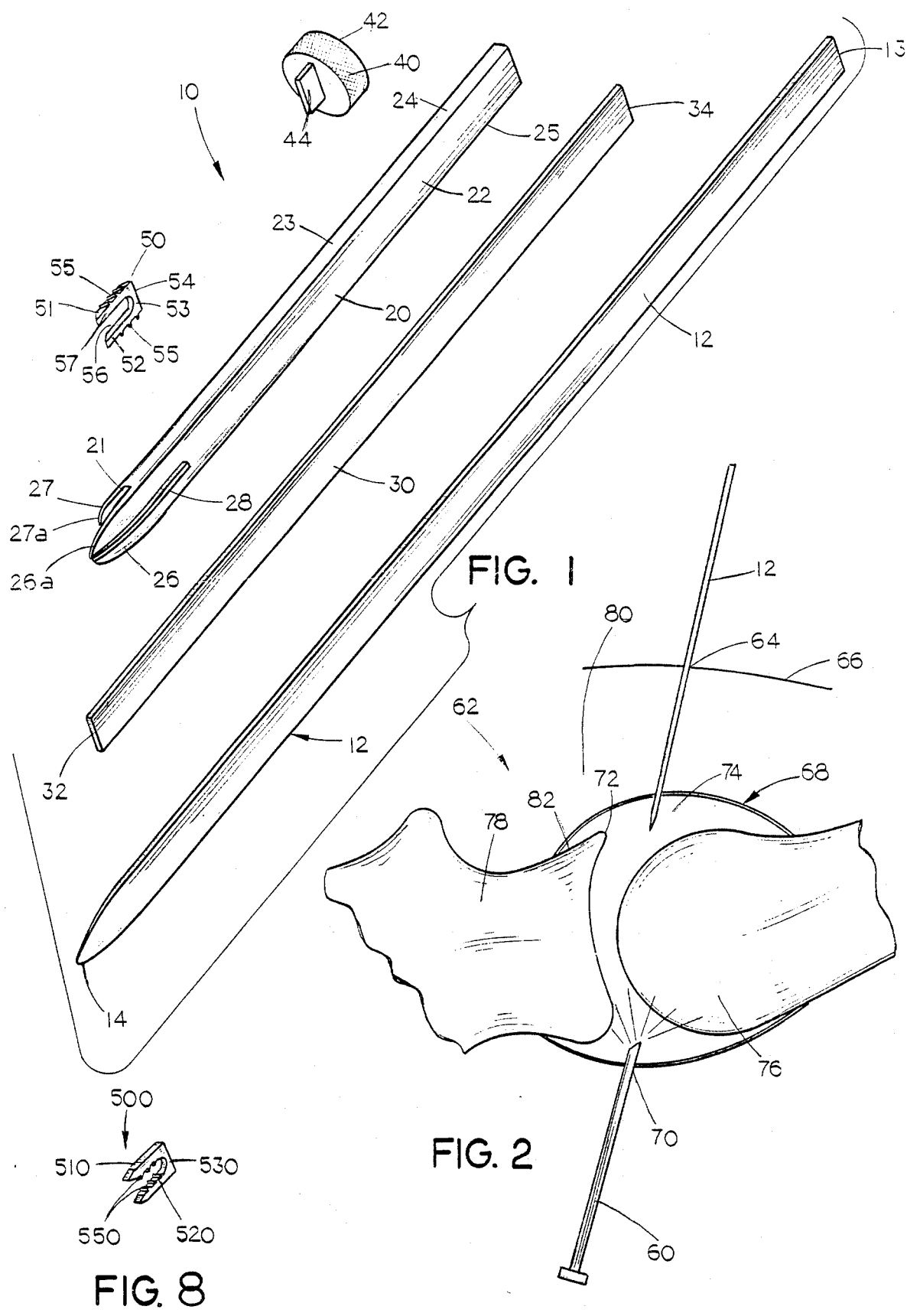

ARTHROSCOPIC SURGICAL INSTRUMENT AND METHOD

BACKGROUND OF THE INVENTION

The present invention is directed generally to an arthroscopic surgical instrument and technique and more specifically to such an instrument and technique for orthopedic surgery relating to capsular stapling for repair of capsular disruption associated with shoulder dislocations and subluxations.

The primary pathology with shoulder dislocation is some type of capsular disruption. The capsular disruption is almost invariably associated with a rip of either the labrum or the capsule off of the scapula or shoulder blade.

A conventional operation for repairing such capsular disruption is an open procedure, called the duToit or Roux. This operation exposes the capsule of the shoulder joint through an open incision and simply puts a tuck in the capsule and staples it in place.

Problems associated with the duToit operation include the usual chance of disease and infection associated with any open surgical procedure, the need for hospitalizing the patient for several days and the asociated time off work and expense of hospitalization.

It is therefore a primary object of the present invention to provide an improved instrument and technique for performing capsular stapling.

Another object is to provide such an instrument and technique whereby the capsular stapling operation may be performed arthroscopically and as an out patient procedure.

Another object is to provide an improved arthroscopic surgical instrument which is simple and durable in construction, economical to manufacture and efficient in operation.

SUMMARY OF THE INVENTION

An arthroscopic surgical instrument for repairing capsular disruption associated with shoulder dislocations and subluxations includes an elongated knife having a sharpened end adapted for insertion through a patient's shoulder girdle and into the shoulder capsule. An elongated sleeve having a sharpened lip protruding from the lower end is telescopically slidable onto and down the knife into the shoulder capsule. A staple is provided which is slidable down through the sleeve upon removal of the knife and a tamper tool is insertable into the sleeve for driving the staple into place.

In the method of the invention, an arthroscope is inserted into the shoulder for viewing the insertion of the knife. The knife is inserted through the interior aspect of the shoulder girdle into the shoulder capsule. The sleeve is then telescopically advanced down the knife to the extent of penetration into the shoulder capsule. Upon withdrawing the knife, a tuck is made in the capsule by moving the penetrated end of the sleeve toward the scapula bone. A tamping block may be placed on the upper end of the sleeve for driving the sleeve into the bone to temporarily hold the tuck. A staple is then placed in the sleeve and followed by a tamper tool for driving the staple through the capsule into the bone to permanently tighten the capsule and thereby decrease the propensity of the shoulder to dislocate.

BRIEF DESCRIPTION OF THE DRAWINGS

FIG. 1 is a perspective view of the parts of the arthroscopic surgical instrument;

FIG. 2 is a diagrammatic illustration of the beginning of the procedure wherein the arthroscope and knife are inserted into the joint;

FIG. 8 is a perspective view of an alternate staple for the invention.

DESCRIPTION OF THE PREFERRED EMBODIMENT

Figure 3:
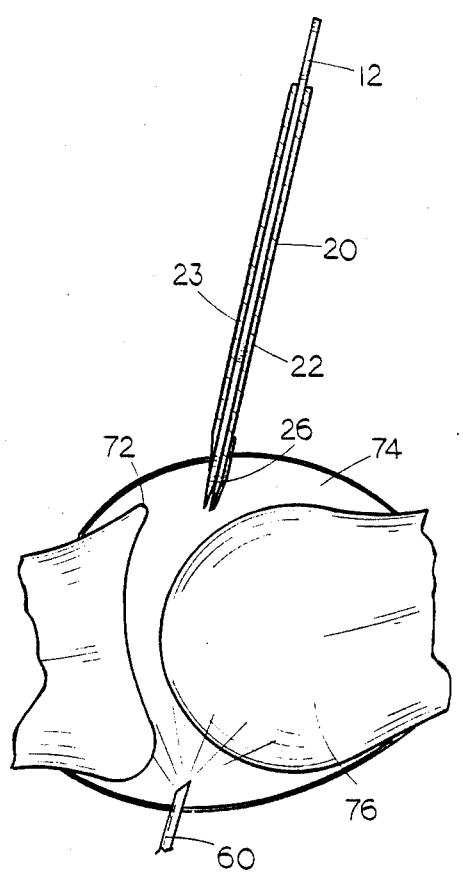
FIG. 3 is a diagrammatic illustration of the placement of the sleeve over the knife to penetrate the capsule.

The arthroscopic surgical instrument 10 of the present invention is shown in FIG. 1 as including an elongated knife 12, a sleeve 20, a tamper tool 30, a tampering block 40 and a staple 50.

Knife 12 is shown as an elongated thin flat blade having one flat blunt end 13 and an opposite rounded sharpened end 14. The knife is an elongated, straight sided member of uniform cross-section throughout the length thereof but for the sharpened end. In the preferred embodiment, the knife is generally rectangular in cross-section, has a width slightly less than 1 centimeter and a length of approximately 25 centimeters. The knife and other parts of the instument should be fabricated from a non-corrosive material such as stainless steel or vitalium.

Sleeve 20 has a longitudinally extended central opening 21 of a size and shape for telescopically receiving the knife 12 in close fitting relation. The sleeve includes a front wall 22, a back wall 23 and opposite side walls 24 and 25 defining a generally rectangle-section sleeve.

The lower ends of front wall 22 and back wall 23 protrude beyond the lower ends of side walls 24 and 25 to define a long lip 26 and short lip 27. The lips are sharpened to closely conform to the knife. Thus, the interior surface of each lip is substantially planar whereas the lower end of the exterior surface tapers downwardly and toward the interior surface to provide a sharpened edge as at 26a and 27a. Long lip 26 is also preferably between ½ and 1 millimeter thicker than the shorter lip for added strength. Furthermore, a longitudianally extended rib 28 having a height and width of approximately 1 millimeter may be formed on the exterior surface of the long lip for additional reinforcement.

The tamper tool 30 is another elongaged straight sided blade having a cross-sectional shape identical to knife 12 but with blunt ends at both ends 32 and 34. The end surfaces are preferably flat and arranged perpendicular to the longitudinal axis of the tool.

The tamping block 40 has a flat top surface 42 arranged perpendicular to a downwardly extended and centrally positioned tab 44 having a cross-sectional size and shape similar to that of the knife 12 and tamper tool 30 so as to fit within the open upper end of the sleeve 20.

Upon insertion of the tab 44 into the upper end of the sleeve, the top surface 42 may be struck with a hammer to drive the sleeve into bone or the like without damage to the top edges of the sleeve.

Staple 50 is shown as a generally U-shaped member having a pair of legs 51 and 52 interconnected by a cross-member 53, preferably having a flat top surface 54 adapted for flush engagement with one end of the tamper tool 30. Barbs 55 are provided on the exterior surface of the legs for retaining the staple in its set position. Staple 50 has a front surface 56 and a back surface 57. The free ends of the legs taper downwardly from the front surface to the back surface.

An alternate form of staple 500 is shown in FIG. 8 as having legs 510 and 520 and a cross member 530. Barbs 550 are provided on the interior surface of the legs and the free end of each leg tapers downwardly and centrally thereof toward a sharpened point.

The following is a description of the procedure for repairing capsular disruption with the instrument 10 of the present invention.

The patient is anesthetized and his shoulder is prepped and draped in the standard fashion. Referring to FIG. 2, an arthroscope 60 is entered into the shoulder 62 from a posterior approach, behind the shoulder, and the shoulder is inspected. After this inspection is done, any intra-articular work that may be necessary is completed.

Knife 12 is then inserted through an approximately 1 centimeter stab wound 64 on the anterior aspect 66 of the shoulder girdle. The knife is advanced into the shoulder until it enters the joint, referred to generally by reference numeral 68. The knife can, of course, be visualized as it enters the joint through the arthroscopic portal 70 posteriorly. The entry point of the knife into the joint should be a given distance, i.e. approximately 178 distal to the edge of the glenoid labrum 72.

Once a satisfactory position has been obtained by the knife 12, the sleeve 20 which fits perfectly flush over the top of the knife, is advanced telescopically down over the knife to enter the shoulder cavity 68. Again, this is visualized from behind with the arthroscope 60.

Figure 4:
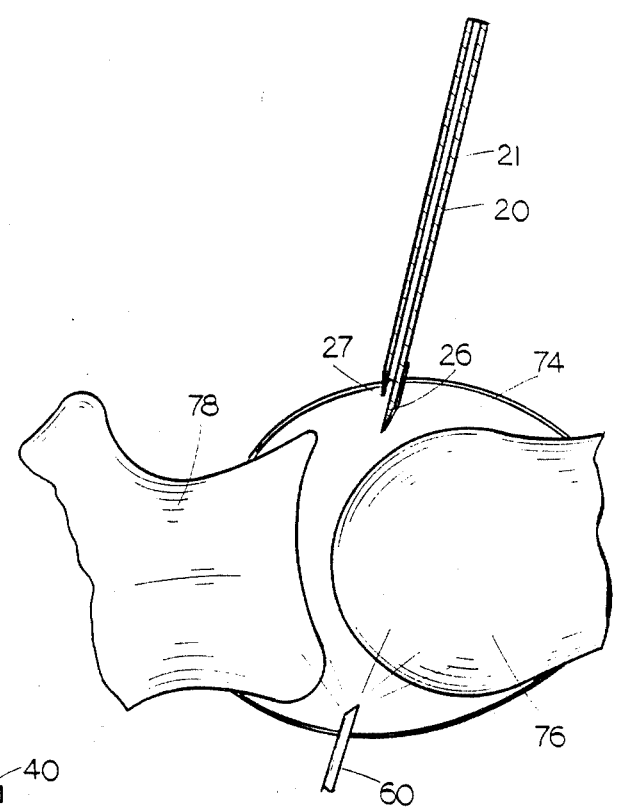
FIG. 4 is a diagrammatic illustration showing the sleeve in position after withdrawal of the knife and prior to partial withdrawal of the shorter sleeve edge.

Referring to FIG. 4, the knife 12 is then removed and only the sleeve 20 remains in the joint. note that both lips 26 and 27 of the sleeve 20 penetrate the capsule prior to removal of the knife. The capsule 74 is the fibrous tissue which holds the arm bone or humerus 76 in the shoulder socket or scapula 78.

The next step is to slightly retract the sleeve from the capsule sufficient for the short lip 27 to slip outside of the shoulder capsule 74. Accordingly, the long lip 26 remains in the capsule 74 while the short lip is outside the capsule with the result that one lip is disposed on either side of the joint capsule 74. The rounded sharpened shape of the short lip 27 allows one to scrape away the capsule from the overlying supraspinatus muscle 80 (FIG. 2), so that just the capsule 74 can be foreshortened.

Figure 5:
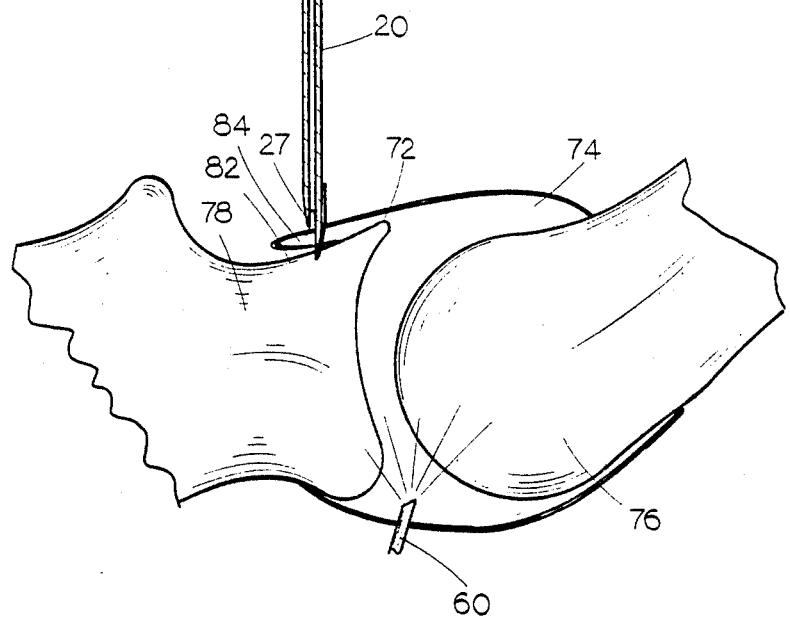
FIG. 5 is a diagrammatic illustration of the sleeve in its moved and set position with the tamper block indicated thereon.

The next step is to put a tuck in the capsule 74, that is to move sleeve 20 from its position a half inch away from the glenoid labrum 72 down to the neck 82 of the scapula 78 as shown in FIG. 5. The moved position of the sleeve can be verified by direct vision, but even more than that, since this procedure is done with the patient lying on his side and his arm partially abducted, a C-arm (fluroscopic X-ray) can be brought in to document the exact placement of the sleeve 20 with reference to the neck of the scapula 78.

Once the tuck 84 has been formed, the tamping block 40 is fitted onto the outer end of the sleeve by inserting tab 44 into the open upper end of the sleeve. The tamping block 40 is firmly struck to tap the long lip 26 of the sleeve into the bone of the neck of the scapula. Note that the capsule 74 has been shortened and gathered up by the trough between the long and short lips 26 and 27 of the sleeve.

Figure 6:
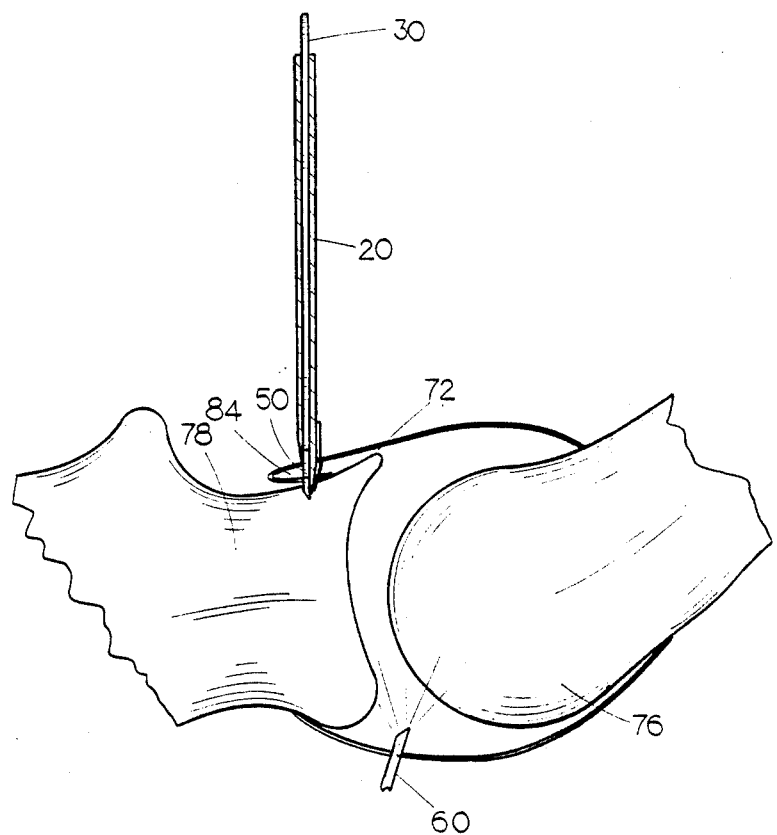
FIG. 6 is a diagrammatic illustration of the sleeve with the staple and hammer inserted therein.
Figure 7:
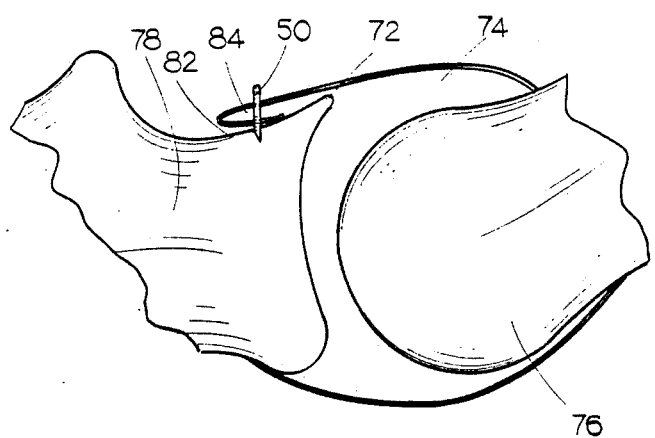
FIG. 7 is a diagrammatic illustration of the completed joint with the stapled capsule.

Referring to FIG. 6, upon removal of the tamping block 40, staple 50 is then dropped into place, legs first. Staple 50 is designed so that the free ends of the legs are beveled from the medial side to the lateral side of the body. Thus it won't skid along the neck of the glenoid. After placing the staple 50 into the rectangular aperture of the sleeve 20, the tamper tool 30 is placed into the same aperture and advanced downwardly to press the staple into the tuck 84. The upper end of the tamping tool 30 is then struck to pound the staple through the capsule 74 and into the scapula 78. The capsule 74 can be roughed up before the staple is pounded firmly down but afterwards, the staple firmly holds the tuck in the capsule. Upon withdrawal of the tamper tool 30 from the sleeve, the sleeve and arthroscope are withdrawn from the shoulder girdle to complete the operation. The capsule has therefore been effectively tightened up, thus decreasing the propensity of the shoulder to dislocate.

Thus there has been shown and described an arthroscopic surgical instrument and procedure which accomplish at least all of the stated objects.

I claim:

1. An arthroscopic surgical instrument for repairing capsular disruption associated with shoulder dislocation and subluxations, comprising,
    an elongated knife having a sharpened end adapted for insertion through a patient's shoulder girdle and into the shoulder capsule,
    an elongated sleeve having a longitudinally extended opening therethrough of a size and shape for telescopically receiving said knife in close fitting relation therein whereby said sleeve may be fitted onto said knife and advanced into the shoulder capsule,
    said sleeve being of shorter length than said knife and including a sharpened lip protruding longitudinally from one end of the sleeve,
    a staple adapted for insertion into the opening of said sleeve for sliding movement therethrough after removal of the knife from said opening, and
    an elongated tamper tool being longer than said sleeve and having opposite blunt ends and a cross sectional shape adapted for sliding movement of said tamper tool through said sleeve whereby, upon engagement of one end of the tamper tool with said staple, the opposite end may be tamped to drive said staple through the capsule into the shoulder blade.

2. The instrument of claim 1 wherein said knife comprises an elongated straight sided member of uniform cross-section throughout the length thereof but for said sharpened end.

3. The instrument of claim 1 wherein said knife and sleeve opening are generally rectangular in cross-section.

4. The instrument of claim 1 further comprising a tamping block having a flat top surface substantially larger than the cross-sectional area of said sleeve and a downwardly extended tab adapted for insertion into the sleeve opening for mounting said tamping block on the sleeve.

5. The instrument of claim 1 wherein said staple comprises a generally U-shaped member including a pair of legs interconnected by a cross member.

6. The instrument of claim 5 wherein the legs of said staple include a plurality of ridges thereon.

7. The instrument of claim 6 wherein said staple includes a front surface and back surface, said legs having lower ends which taper downwardly from the front surface to the back surface.

8. The instrument of claim 6 wherein the free end of each leg of said staple tapers downwardly and centrally thereof toward a sharpened point.

9. The instrument of claim 1 further comprising an elongated elevated ridge adjacent one end of said sleeve, said ridge being connected to and extending along said sharpened lip to reinforce said lip.

10. An orthopedic surgical method of performing capsular stapling arthoscopically, comprising,
providing an arthoscope, an elongated knife having a sharpened end, an elongated sleeve telescopically slidable over the knife and having a sharpened lip at one end, a staple slidable through the sleeve and an elongted tamper tool,
inserting the arthroscope into the shoulder,
inserting the knife through the shoulder girdle into the shoulder capsule,
arthroscopically viewing the insertion of the knife,
placing the sleeve onto the outer end of the knife and telescopcially advancing the sleeve down the knife to the extent of penetration of the sharpened lip of the sleeve into the shoulder capsule,
withdrawing the knife from the sleeve,
making a tuck in the capsule by moving the penetrated end of the sleeve toward the scapula bone,
placing a staple into the sleeve, and
placing one end of the tamper tool into the sleeve and advancing the tool downwardly through the sleeve thereby driving the staple into the capsule.

11. The method of claim 10 wherein the arthroscope is inserted into the shoulder from a posterior approach.

12. The method of claim 12 further comprising arthroscopically inspecting the shoulder prior to insertion of the knife.

13. The method of claim 10 wherein the knife is inserted through a stab wound on the interior aspect of the shoulder girdle.

14. The method of claim 13 wherein the entry point of the knife is approximately one-half inch distal to the edge of the glenoid labrum.

15. The method of claim 10 further comprising arthroscopically viewing the advancement of the sleeve into the shoulder capsule.

16. The method of claim 10 further comprising verifying by direct vision the moved position of the sleeve after making the tuck.

17. The method of claim 10 further comprising verifying by fluoroscopic X-ray the moved position of the sleeve after making the tuck.

18. The method of claim 10 further comprising tapping the sleeve into the scapula bone after making the tuck.

19. An arthroscopic surgical instrument for repairing capsular disruption associated with shoulder dislocation and subluxations, comprising,
an elongated knife having a sharpened end adapted for insertion through a patient's shoulder girdle and into the shoulder capsule,
an elongated sleeve having a longitudinally extended opening therethrough of a size and shape for telescopically receiving said knife in close fitting relation therein whereby said sleeve may be fitted onto said knife and advanced into the shoulder capsule,
said sleeve being of shorter length than said knife and including a sharpened lip protruding longitudinally from one end of the sleeve,
a staple adapted for insertion into the opening of said sleeve for sliding movement therethrough after removal of the knife from said opening, and
an elongated tamper tool being longer than said sleeve and having opposite blunt ends and a cross sectional shape adapted for sliding movement of said tamper tool through said sleeve whereby, upon engagement of one end of the tamper tool with said staple, the opposite end may be tamped to drive said staple through the capsule into the shoulder blade,
said sleeve including a front wall, back wall and side walls, said sharpened lip being an extension of said back wall and further comprising a second lip protruding longitudinally from said front wall, said second lip being shorter than said sharpened lip.

20. The instrument of claim 19 wherein said second lip and sharpened lip each have an interior surface and an exterior surface, the interior surface of both lips being substantially planar and the exterior surface of each lip tapering downwardly towards the interior surface to provide a sharpened edge.

21. An orthopedic surgical method of performing capsular stapling arthroscopically, comprising, providing an arthroscope,
an elongated knife having a sharpened end,
an elongated sleeve telescopically slidable over the knife and having a sharpened lip at one end, a staple slidable through the sleeve and an elongated tamper tool,
inserting the arthroscope into the shoulder,
inserting the knife through the shoulder into the shoulder capsule,
arthroscopically viewing the insertion of the knife,
placing the sleeve onto the outer end of the knife and telescopcially advancing the sleeve down the knife to the extent of penetration of the sharpened lip of the sleeve into the shoulder capsule,
withdrawing the knife from the sleeve,
making a tuck in the capsule by moving the penetrated end of the sleeve toward the scapula bone,
placing a staple into the sleeve, and
placing one end of the tamper tool into the sleeve and advancing the tool downwardly through the sleeve thereby driving the staple into the capsule,
said sleeve having upper and lower ends, said lower end having a short lip spaced apart from the longer aforementioned sharpened lip and wherein the sleeve is telescopically advanced down the knife to the extent of penetration of both lips into the shoulder capsule.

22. The method of claim 21, further comprising retracting said sleeve to withdraw said short lip from said capsule while retaining the longer lip in the capsule.

23. The method of claim 22 further comprising using said short lip to scrape away the capsule from the overlying supraspinatus muscle while making a tuck in the capsule.

* * * * *